United States Patent [19]

Bour et al.

[11] 4,264,501

[45] Apr. 28, 1981

[54] PROCESS FOR THE RECOVERY OF PYRROLIDONE-2

[75] Inventors: Edmond H. J. P. Bour; Sijbrandus E. Schaafsma; Jean M. M. Warnier, all of Geleen, Netherlands

[73] Assignee: Stamicarbon, B.V., Geleen, Netherlands

[21] Appl. No.: 902,884

[22] Filed: May 4, 1978

[30] Foreign Application Priority Data

May 6, 1977 [NL] Netherlands .......................... 7704984

[51] Int. Cl.³ ...................... B01D 3/38; C07D 207/12
[52] U.S. Cl. ............................. 260/326.5 FN; 203/34; 203/35; 260/2.3; 528/490; 528/491
[58] Field of Search ....................... 203/34, 35, 38, 50, 203/61, 96; 159/DIG. 10; 528/326, 486, 490, 500, 501, 491; 260/2.3, 326.5 FN

[56] References Cited

U.S. PATENT DOCUMENTS

| | | | |
|---|---|---|---|
| 2,685,570 | 8/1954 | Verdiers | 260/2.3 |
| 2,828,307 | 3/1958 | Soeterbrock | 260/326.5 FN |
| 3,926,927 | 12/1975 | Stookey | 203/96 |
| 4,187,370 | 2/1980 | Anshus et al. | 528/486 |

FOREIGN PATENT DOCUMENTS 691848  8/1964  Canada ..................................... 260/2.3

*Primary Examiner*—Hiram Bernstein
*Attorney, Agent, or Firm*—Cushman, Darby & Cushman

[57] ABSTRACT

A process is described for the recovery of 2-pyrrolidone monomer from polypyrrolidone waste material by heating the latter in the presence of a small amount of strong acid, and distilling off the said monomer.

6 Claims, No Drawings

PROCESS FOR THE RECOVERY OF PYRROLIDONE-2

The invention relates to a process for the recovery of pyrrolidone-2 from polypyrrolidone.

As is already known, 2-pyrrolidone can be polymerized into polypyrrolidone by means of an anionic catalyst and a suitable promoter, and the resulting polymer can be processed into filaments, films, and other articles. Waste product is, however, obtained in the processing of this polymer, and waste material is also obtained as used up or discarded fabric and articles.

From the view-point of prudent use of raw materials, conservation of energy and for reasons of economy, it would accordingly be advantageous to have a process by which 2-pyrrolidone monomer could be recovered from such polypyrrolidone materials.

According to the present invention, a simple process is now provided whereby 2-pyrrolidone can be obtained from polypyrrolidone by placing the latter in contact with an acid at an elevated temperature and recovering the 2-pyrrolidone that is thereby formed by depolymerization.

It has now been found that the process according to this invention permits the recovery of high-grade monomer from polymeric waste material in a simple way and at low cost.

The temperature at which this process is carried out may be anywhere within the range of from about 100° to 350° C., and particularly between about 175° and 300° C. Thus, it has now been found unexpectedly that the depolymerization reaction can be made to proceed quite excellently, even at temperatures well below the melting point of the polymer. By preference, the temperature employed should be within the range of between 200° C. and the melting point of the polymer, which may be from 255° to 270° C.

In this range the catalyzed depolymerization reaction proceeds very rapidly, and in the absence of thermal depolymerization.

Applicant believes that avoiding thermal depolymerization is advantageous for the objective of formation of high-grade monomer, as it is during thermal depolymerization that the formation of undesirable and contaminating by-products develops.

If the presence of impurities does not matter, e.g., because the recovered monomer will be processed and purified together with virgin monomer, the process according to the invention may also, however, even be carried out at a temperature above the melting point of the polymer starting materials.

The pressure at which the depolymerization is effected is less important to the course of the reaction and from an operative point of view may vary over a wide range, such as between 0.01 and 100 bar. The process is, however, preferably carried out at atmospheric or sub-atmospheric pressure, e.g., at a pressure of from about 0.5 to 1.0 bar. The 2-pyrrolidone monomer is very volatile at these pressures, and hence can be readily recovered.

The depolymerization catalyst employed in this invention may be an organic or inorganic acid or a compound showing an acid reaction, which is itself stable to, and does not itself lead to undesirable secondary reactions under, the reaction conditions used. Preferably, those acid compounds which are used are not or only slightly volatile under the reaction conditions. Such acids should exhibit a boiling point of at least about 225° C. Suitable such acids and acid compounds include the relatively non-volatile mineral acids: phosphoric acid, phosphorous acid, phosphorus pentoxide, sulphuric acid and boric acid, and the high boiling strongly acidic organic acids such as toluene-sulphonic acid, naphthalene-sulphonic acid, trichloracetic acid succinic acid, benzoic acid, phthalic acid, terephthalic acid and citric acid.

Good results are particularly obtained by use of desirably cheap inorganic mineral acids, such as phosphoric acid and sulphuric acid, especially phosphoric acid.

The amount of acid used may range between about only 0.05 and 10% by weight, of the polypyrrolidone to be treated. An amount of about 0.1 to 5.0% by weight is usually sufficient to obtain a proper depolymerization.

Water may also be present in the depolymerization, e.g., either because an aqueous solution of an acid is used as the catalyst, or use is made of polypyrrolidone containing water, or because polypyrrolidone is supplied as an aqueous suspension or slurry of polymer particles. If the reaction is carried out at atmospheric pressure or a lower pressure, the water is soon evaporated. If so desired, distributing agents (which do not induce by-product formation under the reaction conditions) may also be present, e.g., inert organic distributing agents with a high boiling point.

The 2-pyrrolidone product can be recovered by distillation, or stripping, either batch-wise or continuously, from the depolymerization mixture. The monomer so obtained is of excellent quality and can be converted into a very pure monomer suitable for direct use in polymerization reactions by a simple re-distillation purification.

The reaction is preferably carried out in a semi-continuous manner by feeding portion of comminuted polymer and catalyst to the reactor. In the reactor will be an increasing amount of residue, mainly consisting of catalyst, impurities introduced with the polymer and high-boiling byproducts. From time to time the residue is discharged, and it is preferred to increase the temperature in the reactor to between 275° C. and 300° C. before such discharging.

The preferred means of heating the reaction mass is by the introduction of superheated steam in the reaction mass, while maintaining a pressure of between 0.70 and 0.95 bar in the reactor. Under these conditions there is no need for mechanical stirring and the pyrrolidone is quickly stripped from the reaction mass. The resulting mixture of steam and pyrrolidone may be condensed by cooling, yielding a rather diluted aqueous solution of pyrrolidone. It is preferred to subject the vapours to a rectification or fractioned distillation, in order to obtain to a more concentrated solution of pyrrolidone, in a concentration of e.g. between 30 and 70% by weight of pyrrolidone.

The starting materials may be pure polypyrrolidone, e.g., as waste or scrap product obtained from polymerization processes, or in the purification and processing of the polymer, or from fibers or woven fabric. Use may also be made of polymers and oligomers or low molecular weights. Copolymers and mixtures with other polymers, such as cotton, polyester, polycaprolactam or wool, may also be used. If so desired, the starting material may first be ground or cut and/or freed from impurities, such as spinning agents, sizings and the like.

The invention is now further illustrated by the following Examples, without, however, being restricted to these specific embodiments.

EXAMPLES

EXAMPLE 1

A glass flask was provided with a heating jacket, a gas outlet with condensing means, and was connected to a vacuum pump. A mixture of 20 grams of finely ground polypyrrolidone (relative viscosity 21 in sulphuric acid) and 0.08 gram of phosphoric acid was heated at 215° to 220° C. in the flask for 30 minutes at a pressure of 0.013 bar.

Upon cooling, the recovered condensed vapor yielded 18.2 grams of 2-pyrrolidone having a purity of over 95%.

EXAMPLE 2

The process of Example 1 was repeated, but with the use of 0.10 gram of concentrated sulphuric acid as the catalyst. 12.8 grams of 2-pyrrolidone were obtained in only 30 minutes, of a purity of about 96%.

EXAMPLE 3

The process of Example 1 was repeated, but at a pressure of 0.8 bar at a temperature of 210° to 215° C., and with the use of 0.14 grams of toluene-sulphonic acid (technical ortho/para mixture) as the catalyst. 12.6 grams of substantially pure 2-pyrrolidone monomer were now obtained in 30 minutes.

EXAMPLE 4

The process of Example 1 was repeated, but under 1.01 bar and at a temperature of 260° to 265° C., with the use of 0.14 gram of terephthalic acid as the catalyst. 8.7 grams of substantially pure 2-pyrrolidone were now obtained in 30 minutes.

The process of the foregoing Examples can also be used with the other acids named hereinabove.

What is claimed is:

1. A process for the recovery of 2-pyrrolidone monomer from polypyrrolidone starting materials which consists essentially in treating said starting materials with from about 0.05 to about 10 percent by weight of the polypyrrolidone, an inorganic or organic acid compound having a boiling point of at least 225° C., then heating at a temperature between about 200° C. and the melting point of said starting material and recovering the resultant pyrrolidone-2 monomer by distillation.

2. Process according to claim 1, wherein said treatment is effected at a pressure of between about 0.5 and 1.0 bar.

3. Process according to claim 1, wherein said acid compound is used in an amount of between about 0.1 and 5.0% by weight, based on the polypyrrolidone.

4. Process according to claim 1, wherein said acid compound is selected from the group consisting of phosphoric acid, phosphorous acid, boric acid, sulphuric acid, mono- and bi-cyclic aromatic sulphonic acids and aliphatic and aromatic mono-, di- and tri-carboxylic acids.

5. Process according to claim 1, wherein said acid compound is phosphoric acid.

6. Process for the recovery of 2-pyrrolidone monomer from polypyrrolidone starting materials, wherein said starting material is heated to a temperature of between 200° C. and the melting point of the starting material at a pressure of between 0.5 and 0.95 bar in the presence of between 0.1 and 10% weight of a strong inorganic acid, having a boiling point of at least 225° C. the reaction mixture being heated by the introduction of superheated steam therein, and recovering 2-pyrrolidone as an aqeous solution by condensation of the vapor mixture, optionally under rectifying conditions.

* * * * *